United States Patent
Maestri et al.

(10) Patent No.: US 10,610,476 B2
(45) Date of Patent: *Apr. 7, 2020

(54) COSMETIC COMPOSITIONS OF UV FILTERS

(71) Applicant: 3V Sigma S.P.A., Milan (IT)

(72) Inventors: Francesco Maestri, Bergamo (IT); Ferruccio Berte', Bergamo (IT)

(73) Assignee: 3V Sigma S.P.A., Milan (IT)

( * ) Notice: Subject to any disclaimer, the term of this patent is extended or adjusted under 35 U.S.C. 154(b) by 6 days.

This patent is subject to a terminal disclaimer.

(21) Appl. No.: 15/658,444

(22) Filed: Jul. 25, 2017

(65) Prior Publication Data

US 2018/0028425 A1 Feb. 1, 2018

(30) Foreign Application Priority Data

Jul. 29, 2016 (IT) .................. 102016000080304

(51) Int. Cl.
| | | |
|---|---|---|
| *A61K 8/49* | (2006.01) | |
| *A61K 8/37* | (2006.01) | |
| *A61K 8/35* | (2006.01) | |
| *A61Q 17/04* | (2006.01) | |
| *A61K 8/06* | (2006.01) | |
| *A61K 8/40* | (2006.01) | |

(52) U.S. Cl.
CPC ............. *A61K 8/4966* (2013.01); *A61K 8/06* (2013.01); *A61K 8/35* (2013.01); *A61K 8/37* (2013.01); *A61K 8/40* (2013.01); *A61Q 17/04* (2013.01)

(58) Field of Classification Search
None
See application file for complete search history.

(56) References Cited

U.S. PATENT DOCUMENTS

| 2,415,554 | A | 2/1947 | Friedheim | |
|---|---|---|---|---|
| 6,193,960 | B1 * | 2/2001 | Metzger | A61K 8/4966 |
| | | | | 424/400 |
| 2018/0030001 | A1 * | 2/2018 | Maestri | A61K 8/4966 |

FOREIGN PATENT DOCUMENTS

| EP | 0818450 A1 | 1/1998 |
|---|---|---|
| EP | 0821938 A1 | 2/1998 |

OTHER PUBLICATIONS

Search Report and Written Opinion of IT 2016000080304 dated Mar. 21, 2017.

* cited by examiner

*Primary Examiner* — Erin E Hirt
(74) *Attorney, Agent, or Firm* — Silvia Salvadori, P.C.; Silvia Salvadori

(57) ABSTRACT

The present invention relates to cosmetic compositions comprising a combination of at least one triazine compound of general formula (I):

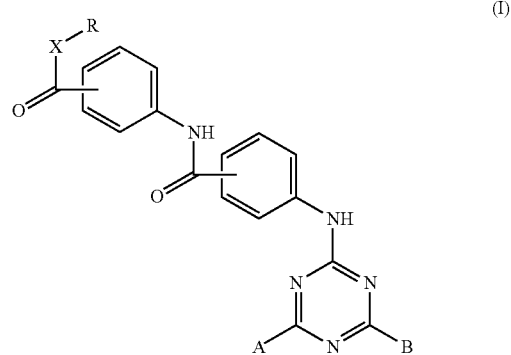

wherein A, B, X and R are as defined in the description, with other cosmetic sunscreens.

7 Claims, No Drawings

COSMETIC COMPOSITIONS OF UV FILTERS

This application claims priority to and the benefit of Italian Application No. 102016000080304 filed Jul. 29, 2016 the content of which is incorporated herein by reference in its entirety.

The present invention relates to new cosmetic compositions designed to protect the skin and hair against UV radiation.

PRIOR ART

Ultraviolet solar radiation has a damaging effect on skin tissue, and causes the degradation of polymers. By using particular compounds called sunscreens, which absorb the UV part of solar radiation, harmful effects and aging of the skin and polymer materials can be prevented, or at least slowed.

Numerous substances have been studied and tested as protective agents, and a great deal of patent literature now exists relating to compounds belonging to various chemical classes that absorb in the ultraviolet region, particularly radiation between 290 and 320 nm, called UV-B, and between 320 nm and 400 nm, called UV-A.

Relatively few of these compounds have proved suitable for practical application.

A drawback shared by all these compounds is their low ability to absorb radiation, which means that relatively large quantities are required to obtain the optimum photoprotective effect.

An excellent UV-B or UV-A absorber should have the following characteristics:
1) High specific extinction $E^1_1$ allowing the use of low doses, resulting in cost savings and minimal toxicological risk
2) Light stability
3) Heat stability
4) Oxidation stability
5) Stability to different pHs
6) Good solubility in the basic substances commonly used for dermatological formulations
7) Negligible toxicity
8) Colour and odour compatible with the intended applications
9) High molecular weight, which reduces the probability of absorption by the skin and increases toxicological safety
10) Compatibility with the various substances generally used in dermatological formulations.

The concentrations of UV-absorber solutions are characterised by the parameter $E^1_1$ (or E11), which corresponds to the specific extinction value measured at the maximum absorption wavelength of a solution containing 1% of the product in question, measured with an optical path of 1 cm.

Numerous derivatives of symmetrical triazine are already known, which can be used in a wide variety of technical applications and sectors due to their properties of absorbing UV rays, in particular UVA and UVB rays. Examples of said triazines are disclosed in DE 3206398, U.S. Pat. Nos. 4,617,390, 4,724,137, 5,233,040, 5,252,323, 5,332,568, IT 1255729, U.S. Pat. Nos. 5,346,691, 5,393,517, EP 832642, U.S. Pat. Nos. 5,744,127, 5,759,525, 5,801,244, 6,018,044, 6,193,960, US 2002085981 and US 2005143577.

In particular, DE 3206398 discloses s-triazine derivatives obtained by reacting trichlorotriazine with p-amino-benzoic acid esters, which absorb intensely in the UV-B region. Unfortunately, the solubility of said compounds in the solvents generally used to formulate sun creams is very low, which makes their practical use problematic and very difficult, especially when the percentage of photoprotector in the composition must be increased to prepare formulations with a high sun protection factor.

IT 1255729 discloses s-triazine derivatives obtained by reacting trichlorotriazine with p-amino-benzoic acid esters or amides with high specific extinction in the UV-B zone and improved solubility in solvents.

EP 832642 discloses s-triazine derivatives obtained by reacting trichlorotriazine with p-aminophenyl-benzoxazole derivatives with high specific extinction in the UV-A zone and improved solubility in solvents.

Sun protection factor (SPF) is a measurement of the photoprotective power of a sunscreen or a cosmetic formulation containing one or more sunscreens. The sun protection factor is the ratio between the MED (Minimal Erythema Dose) determined on protected skin and the MED determined on unprotected skin. It is directly correlated with specific extinction, and therefore also with the amount of photoprotector present in the cosmetic preparation.

However, the UV protection which a single sunscreen can contribute generally falls into a wavelength band which is too narrow in relation to the UV spectrum of natural light to which the skin and hair are normally exposed. For this main reason a combination of a plurality of sunscreens able to provide broad protection against both UVA and UVB is used. Combinations of a plurality of sunscreens in cosmetic formulas are also necessary to impart other essential or desirable properties, such as:
1) high absorption in a broad UV spectrum
2) photo- and heat-stability
3) compatibility with the skin (not harmful or dangerous)
4) good adherence and skin feel
5) water resistance
6) good compatibility with other cosmetic substances.

DESCRIPTION OF THE INVENTION

The present invention relates to cosmetic compositions for topical use designed to protect the skin and/or hair against UV radiation, comprising:
a) at least one UV filter of formula (I),

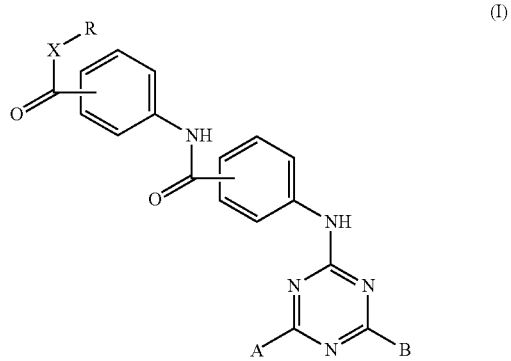

wherein:
X is an —O— or —NH— group
R is a straight, cyclic or branched $C_1$-$C_{18}$ alkyl group
and groups A and B can be, independently of one another:
a group of formula (II)

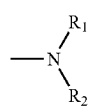

wherein $R_1$ and $R_2$ can be, independently of one another, H, straight, cyclic or branched $C_1$-$C_{22}$ alkyls or $C_1$-$C_{18}$ hydroxyalkyls, $C_2$-$C_{18}$ alkoxyxalkyls, or polyalkylene glycols;

or a group of formula (III)

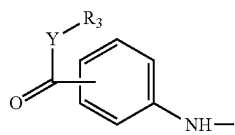

wherein Y, independently of the value of X, is an —O— or —NH— group $R_3$ is a straight, cyclic or branched $C_1$-$C_{18}$ alkyl group which is the same or different from R;

or a group of formula (IV)

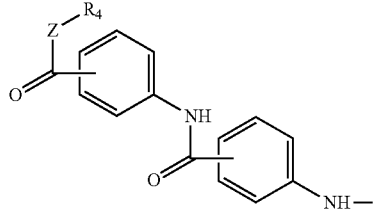

wherein Z, independently of the value of X or Y, is an —O— or —NH— group $R_4$ is a straight, cyclic or branched $C_1$-$C_{18}$ alkyl group which is the same or different from R and $R_3$;

b) at least one other UV filter selected from 2-ethylhexyl p-methoxycinnamate, 2-hydroxy-4-methoxybenzophenone, 2-hydroxy-4-methoxybenzophenone-5-sulphonic acid, ethylhexyl salicylate, ethylhexyl dimethyl PABA, drometrizole trisiloxane, 3-(4'-methylbenzylidene)-d,l-camphor, diethylhexyl butamido triazone, ethylhexyl triazone, 4-(tert-butyl)-4'-methoxy-dibenzoylmethane, 2-cyano-3,3-diphenylacrylic acid 2-ethylhexyl ester, bis-ethylhexyloxyphenol-methoxyphenyl-triazine, methylene-bis-benzotriazolyl-tetramethyl-butylphenol, benzoic acid 2-(4-diethylamino-2-hydroxybenzoyl)-hexyl ester, 2,4-bis-[4-[5-(1,1-dimethyl-propyl) benzoxazol-2-yl]phenylimino]-6-[(2-ethylhexyl)-imino]-1,3,5-triazine, tris-biphenyltriazine, titanium dioxide and zinc oxide;

c) optionally other components such as solvents, diluents, auxiliaries and carriers normally used in the cosmetic field.

Cosmetic products or preparations usually contain compounds (a) and (b) in quantities of up to 20% by weight of the formulation, together with carriers or diluents normally used in this field, with or without the conventional auxiliary additives.

Component (a) of the compositions of the invention preferably consists of one or more compounds of formula (I) wherein the carboxylate —CO—O— or amide —CO—NH— (or also —CO—X—, —CO—Y—, —CO—Z—) groups on the phenyl rings occupy the para or 4 position relative to the —NH— group, and the R, $R_1$, $R_2$, $R_3$ and $R_4$ groups are straight or branched $C_1$-$C_{12}$ alkyl groups.

Even more preferably, component (a) of the compositions of the invention is selected from the compounds of formula (V), (VI) and (VII)

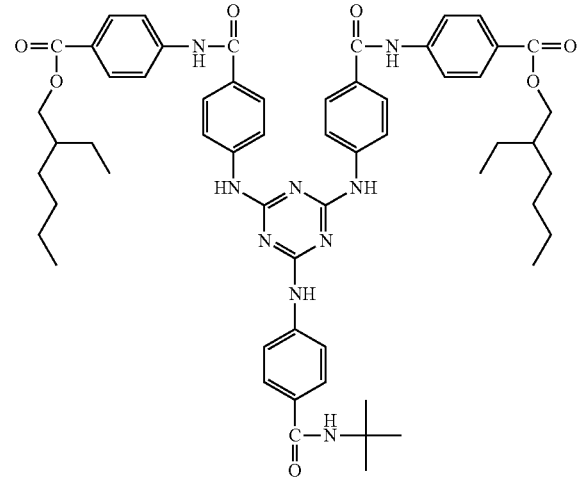

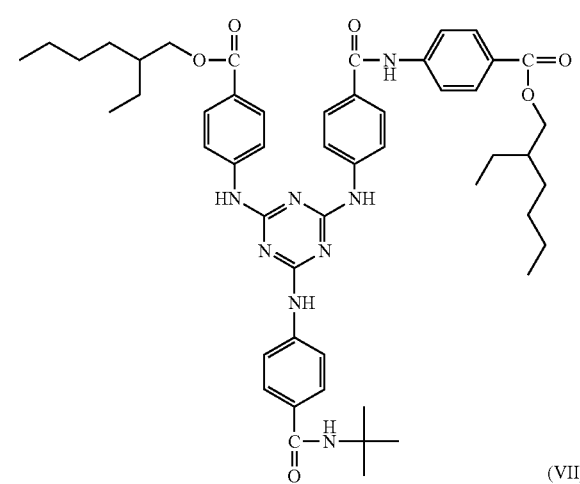

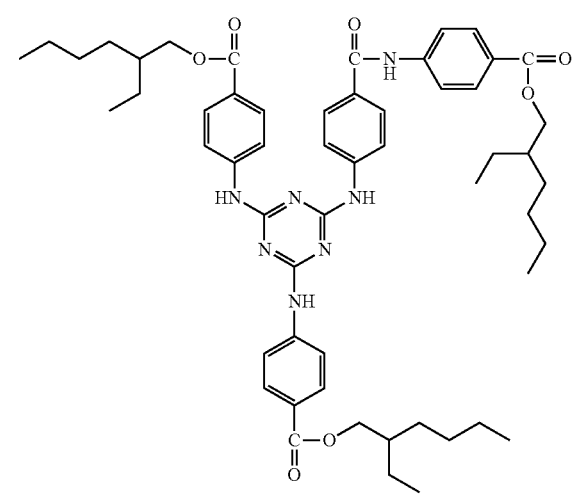

The compounds constituting component a) of the invention, in addition to high absorption in both the UV-B and the UV-A region, also have other advantageous characteristics, such as heat stability and lack of toxicity, due to their very high molecular weight.

Typically, the numerical UV-A/UV-B ratio of these compounds, defined as the ratio of the intensity of the radiation absorbed between 320 nm and 400 nm (UVA fraction) to that absorbed between 290 nm and 320 nm (UVB fraction), is greater than 0.20, preferably greater than 0.30, whereas in the analogous triazine compounds with a 4-aminobenzoate or 4-aminobenzamide substituent different from the substituents described in Formula (IV), it is below about 0.14. Moreover, we have found that by increasing the number of substituents of formula (IV) in the compounds of formula (I), the UV-A light absorption component increases accordingly. The fact that it possesses a significant UV-A component and therefore a broader UV spectrum is undoubtedly an advantage for a substance intended for use as a sunscreen.

The compounds of formulas (I)-(VII) can be prepared by reacting a nitrobenzoyl chloride or bromide with compounds of formula (VIII)

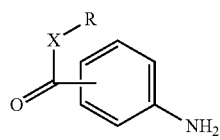
(VIII)

to generate the nitro intermediate of formula (IX)

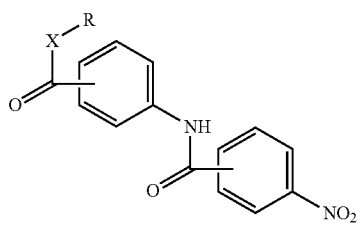
(IX)

which, by subsequent reduction or hydrogenation, affords an amino intermediate (X).

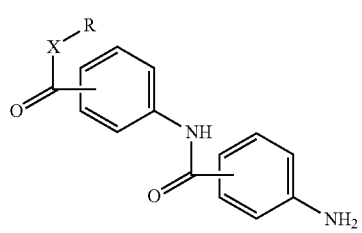
(X)

Intermediate (X) is then reacted with cyanuryl chloride or bromide according to the most suitable stoichiometries and sequences based on well-known synthesis techniques.

The compounds of formula (I) must therefore necessarily be prepared by reacting 1 mole of cyanuryl chloride or bromide with at least 1 mole of intermediate (X), and optionally, where appropriate, with the remaining moles of amino compounds of formula (VIII) and/or (XI), wherein the amines of formula (XI) are:

(XI)

wherein $R_1$ and $R_2$ maintain the meaning described above.

The order in which intermediate (X) and optionally the amines of formula (VIII) and/or (XI) are reacted with cyanuryl chloride or bromide can follow any intermediate sequence and stoichiometry.

Cyanuryl chloride and bromide have three reactive halogen atoms able to react selectively with ammonia, primary amines and secondary amines at very different temperatures, thus making it possible to replace each halogen atom with the desired amine with quantitative yields.

The subsequent synthesis for the preparation of triazine compounds from amino intermediates such as aminobenzoates and aminobenzamides is well known, and described, for example, in DE 3206398, U.S. Pat. Nos. 4,617,390, 4,724,137, 5,233,040, 5,252,323, 5,332,568, IT 1255729, U.S. Pat. Nos. 5,346,691, 5,393,517, EP 832642, U.S. Pat. Nos. 5,744,127, 5,759,525, 5,801,244, 6,018,044, 6,193,960, US 2002085981 and US 2005143577.

As the reaction produces acidity, neutralising bases are used in many cases, optionally in an aqueous medium, such as sodium hydroxide, sodium carbonate, sodium bicarbonate, calcium hydroxide, calcium carbonate, and tertiary amines such as triethylamine or pyridine.

The solvents wherein the compounds of the invention can be prepared need not be able to dissolve the compounds. However, it is essential that they do not interact chemically with the compounds under the reaction conditions. In this respect they must be inert. Examples of solvents which can be used are saturated linear and branched hydrocarbons such as hexane, cyclohexane, methylcyclohexane, heptane, octane, isooctane, decane, petrols and dearomatised white spirits, aromatic hydrocarbons such as benzene, toluene, xylenes, ethylbenzene and petrols and white spirits, also containing aromatic hydrocarbons, ketones such as acetone, methyl ethyl ketone, methyl isobutyl ketone and diisobutyl ketone, ethers such as tetrahydrofuran and dioxane, esters such as ethyl acetate and butyl acetate, and nitriles such as acetonitrile and benzonitrile.

The operating temperatures are from 0° C. to 200° C., preferably from 40 to 150° C. The pressures can range from 0 to 50 bars, preferably from 0 to 5 bars.

Component (b) of the compositions of the invention is selected from one or more UVA and UVB sunscreens such as those listed in Annex VII to the European Cosmetics Directive (76/768/EEC) and Annex VI to European Regulation (EC) No. 1223/2009, as amended, in Household and Personal Care Monographic Special Issue Skin Care—"The encyclopedia of allowed sunfilters in the world" by Giulio Pirotta, Consultant, via Solferino 4, 21040 Uboldo (VA) Italy and in ELECTRONIC CODE OF FEDERAL REGULATIONS (FDA) PART 352—SUNSCREEN DRUG PRODUCTS FOR OVER-THE-COUNTER HUMAN USE; Subpart B—Active Ingredients. The physical form of some sunscreens which are poorly soluble or insoluble in cosmetic formulations, such as zinc oxide, titanium dioxide, bis-ethylhexyloxyphenol-methoxyphenyl-triazine, methylene-bis-benzotriazolyl-tetramethylbutylphenol and tris-biphenyltriazine, can be a nano form or a form finely subdivided and stably dispersed in the formulation.

Examples of auxiliaries normally used in cosmetics and useful as additives are emulsifiers, such as ethoxylated fatty alcohols, fatty acid esters with sorbitan or lanolin derivatives, thickeners or rheology modifiers, such as carboxymethylcellulose or crosslinked polyacrylic acids, preservatives and perfumes.

Other auxiliaries are stabilisers such as magnesium or aluminium salts of fatty acids, complexing agents such as EDTA, and antioxidants such as BHT, BHA or alpha-tocopherol.

The cosmetic oils used as auxiliaries are, for example, isopropyl esters of fatty acids, in particular isopropyl stearate, isopropyl palmitate, isopropyl isostearate, isopropyl myristate, isopropyl laurate, liquid paraffin, vaseline, isoparaffins and mineral oil.

Other ingredients of the cosmetic compositions of the invention can be cosmetic agents such as panthenol, bisabolol, alpha-tocopherol, alpha-tocopherol acetate, Aloe vera, seaweed extracts and hyaluronic acid.

Examples of bases for UV cosmetic compositions in the form of oil comprise vegetable oils such as groundnut oil, olive oil, sesame oil, cottonseed oil, coconut oil, grapeseed oil, castor oil, or mineral oils, such as liquid petrolatum or, in particular, liquid paraffin, synthetic esters of fatty acids and glycerides. Examples of bases for ointments are petrolatum, lanolin, eucerin and polyethylene glycols.

Examples of bases for creams are creams with a high fat content, glycerol, creams based on polysaccharides and modified cellulose such as Tylose and, for creams based on fats and waxes, cetyl alcohol, lanolin cream, cocoa butter, beeswax, stearic acid, stearyl alcohol, glycerol monostearate, natural oils and minerals and fats.

Examples of bases for emulsions are mixtures of stearyl glycol, a vegetable and/or mineral oil such as almond oil, liquid paraffin and petrolatum, water or mixtures of ethyl alcohol, water, lanolin, tragacanth or mixtures of ethyl alcohol, stearin, water, tragacanth and glycerol or mixtures of stearic acid, liquid paraffin, propyl or isopropyl alcohol and water.

The nature of the carrier, auxiliaries or diluents determines the final physical form of the cosmetic compositions containing the sunscreens. The compositions can be in the form of a solution, oil, cream, ointment, lotion, gel or powder.

Preparations and ingredients of these types can be found, for example, in "Sunscreens: Development: Evaluation, and Regulatory Aspects." Nicholas J. Lowe, $2^{nd}$ Edition; Manuale del Cosmetologo, Giovanni D'Agostinis, Elio Mignini, 2014; "Seifen, Ole, Fette, Wachse", (1955), p. 147 and European Cosmetic Ingredients Inventory (CosIng).

The invention also relates to the use of said compounds as sunscreens for the skin and hair, due to their ability to perform a surprising skin protection action against the harmful component of solar radiation.

The invention will now be illustrated by the following examples. All quantities are given in grams.

Example 1

Compounds (V), (VI) and (VII) were tested for their ability to perform a photoprotective action. Said compounds were added to standard cosmetic formulas (formulas shown in Table 1) to evaluate the SPF value (sun protection factor) with a Labsphere UV-20005 instrument, in the UV-visible region from 290 to 400 nm. For the experimental measurement of the SPF, the cosmetic formula was applied to a Transpore medium (3M Inc.) at a concentration of 2.0 mg/cm$^2$. 3 tapes were prepared for each formula, 12 readings per tape being conducted; readings with a covariance >10% above the average were rejected. The SPF data are set out in Table 2.

TABLE 1

| Phase | Ingredient | INCI name | Formula 1 | Formula 2 | Formula 2 |
|---|---|---|---|---|---|
| A1 | Water | water | 72.5 | 72.5 | 72.5 |
| A1 | Propylene Glycol | propylene glycol | 1 | 1 | 1 |
| A2 | Satiaxane CX91 | xanthan gum | 0.6 | 0.6 | 0.6 |
| A2 | Ultrez 10 | Carbomer | 0.15 | 0.15 | 0.15 |
| A2 | Disodium EDTA | disodium EDTA | 0.08 | 0.08 | 0.08 |
| B1 | Lanette 16 | cetyl alcohol | 1 | 1 | 1 |
| B1 | Tego alkanol S21P | steareth-21 | 2.5 | 2.5 | 2.5 |
| B1 | Tego alkanol S2P | steareth-2 | 3 | 3 | 3 |
| B1 | Cetiol CC | dicaprylyl carbonate | 6.5 | 6.5 | 6.5 |
| B1 | Tegosoft DC | decyl cocoate | 6.5 | 6.5 | 6.5 |
| B2 | Compound of formula (V) | | 1 | | |
| B2 | Compound of formula (VI) | | | 1 | |
| B2 | Compound of formula (VII) | | | | 1 |
| C | TEA | TEA | 0.225 | 0.225 | 0.225 |
| D | Dow Corning 245 | cyclomethicone | 2 | 2 | 2 |
| D | Microcare PMS | phenoxyethanol and paraben | 1 | 1 | 1 |

Preparation: Phase B1 was heated to 70°-75° C. under stirring, and B2 was then added. A1 was heated separately to 70°-75° C., adding phase A2 and homogenising with a turboemulsifier. Maintaining the temperature at 70°-75° C., B1+B2 was poured into A1, and homogenised with a turboemulsifier. After adding C, the formulation was cooled to 40° C., and phase D was then added, again under stirring.

TABLE 2

| Formula | Mean SPF | UVA:UVB ratio | Critical wavelength |
|---|---|---|---|
| 1 | 3.50 | 0.58 | 314.0 |
| 2 | 3.21 | 0.33 | 311.0 |
| 3 | 3.15 | 0.35 | 313.0 |

The UVA:UVB ratio is the ratio between the intensity of the radiation absorbed between 320 nm and 400 nm (UVA fraction) and that absorbed between 290 nm and 320 nm (UVB fraction). The UVA fraction of the compounds of formulas (V), (VI) and (VII) of the invention is at least twice as high as those of the triazine analogues already known, such as diethylhexyl butamido triazone and ethylhexyl triazone, for which said ratio is between 0.12 and 0.14.

Example 2

| Sun oil | |
|---|---|
| INCI DECLARATION | % |
| Ethanol | Up to 100 |
| Cetearyl Octanoate | 10.0 |
| $C_{12-15}$ Alkyl Benzoate | 15.0 |
| Cyclomethicone | 35.0 |
| Tocopheryl Acetate | 0.8 |
| Tocopherol (and) Lecithin (and) Ascorbyl Palmitate (and) Citric Acid | 0.05 |
| Compound (VI) | 4.0 |
| Octocrylene | 6.0 |
| ButylMethoxydibenzoylmethane | 3.6 |
| Ethylhexyl Methoxycinnamate | 0.5 |
| Bis-Ethylhexyloxyphenol Methoxyphenyl Triazine | 1.5 |
| SPF in vitro | 32.0 |
| SPF in vitro with ethylhexyl triazone instead of the compound of formula (VI) | 25.2 |

Example 3

| Sun cream | |
|---|---|
| INCI DECLARATION | % |
| PEG-7 Hydrogenated castor oil | 6 |
| Isopropyl palmitate | 5 |
| Mineral oil | 10 |
| Caprylic/Capric Triglyceride | 3 |
| Magnesium Stearate | 0.6 |
| Compound (V) | 1 |
| Diethylhexyl butamido triazone | 1 |
| Octocrylene | 3 |
| Tocopheryl Acetate | 0.5 |
| PEG-45/dodecyl Glycol Copolymer | 2 |
| Aqua | up to 100 |
| Glycerin | 0.3 |
| Magnesium Stearate | 0.3 |
| Methylparaben | 0.2 |
| Propylparaben | 0.2 |
| SPF in vitro | 9.2 |
| SPF in vitro with diethylhexyl butamido triazone instead of the compound of formula (V) | 4.0 |

Example 4

| Sun milk | |
|---|---|
| INCI DECLARATION | % |
| PEG-7 Hydrogenated castor oil | 6 |
| Hydrogenated Castor oil | 0.5 |
| Mineral oil | 5 |
| EthylhexylMethoxycinnamate | 10 |
| Isoamyl p-Methoxycinnamate | 5 |
| Compound (VII) | 2 |
| ButylMethoxydibenzoylmethane | 2 |
| Titanium dioxide | 6 |
| Tocopheryl Acetate | 0.5 |
| Peg-45/dodecyl glycol copolymer | 2 |
| Dimethicone | 1 |
| 4-Methylbenzilidene camphor | 3 |

-continued

| Sun milk | |
|---|---|
| INCI DECLARATION | % |
| Aqua | Up to 100 |
| Propyl glycol | 5 |
| Disodium EDTA | 0.5 |
| Phenoxyethanol | 0.5 |
| SPF in vitro | 31.5 |
| SPF in vitro with ethylhexyl triazone instead of the compound of formula (VII) | 24.0 |

Example 5

| Sun milk | |
|---|---|
| INCI DECLARATION | % |
| PEG-7 Hydrogenated castor oil | 6 |
| Hydrogenated Castor oil | 0.5 |
| Mineral oil | 5 |
| EthylhexylMethoxycinnamate | 10 |
| Isoamyl p-Methoxycinnamate | 5 |
| Compound (VII) | 1 |
| Ethylhexyl Triazone | 1 |
| ButylMethoxydibenzoylmethane | 2 |
| Titanium dioxide | 6 |
| Tocopheryl Acetate | 0.5 |
| Peg-45/dodecyl glycol copolymer | 2 |
| Dimethicone | 1 |
| 4-Methylbenzilidene camphor | 3 |
| Aqua | Up to 100 |
| Propyl glycol | 5 |
| Disodium EDTA | 0.5 |
| Phenoxyethanol | 0.5 |
| SPF in vitro | 28.3 |
| SPF in vitro with ethylhexyl triazone instead of the compound of formula (VII) | 24.0 |

Example 6

| Spray-on sun lotion | |
|---|---|
| INCI DECLARATION | % |
| Aqua | up to 100 |
| Glycerin | 3 |
| Acrylates/Vinyl Isodecanoate Crosspolymer | 0.2 |
| PEG-100 Distearate & Glyceryl Stearate | 2 |
| Cetearyl Alcohol | 0.5 |
| C12-15 Alkyl Benzoate | 18 |
| Compound (VI) | 3.5 |
| Bis-Ethylhexyloxyphenol Methoxyphenyl Triazine | 1.5 |
| ButylMethoxydibenzoylmethane | 1 |
| TEA | at pH 6.3 |
| Cyclomethicone | 3 |
| Phenoxyethanol | 0.5 |
| SPF in vitro | 19.0 |
| SPF in vitro with ethylhexyl triazone instead of the compound of formula (VI) | 13.8 |

The invention claimed is:
1. Cosmetic compositions for topical use comprising:
a) at least one UV filter of formula (I),

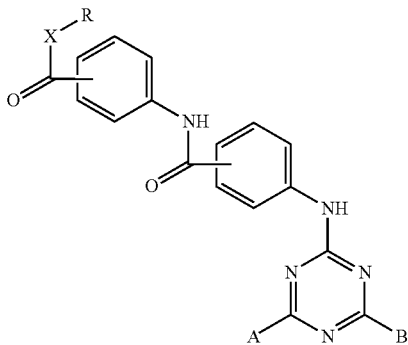

wherein:
X is an —O— or —NH— group
R is a straight, cyclic or branched $C_1$-$C_{18}$ alkyl group
and groups A and B are, independently of one another:
a group of formula (II)

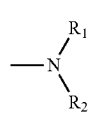

wherein $R_1$ and $R_2$ are, independently of one another, H, straight, cyclic or branched $C_1$-$C_{22}$ alkyls or $C_1$-$C_{18}$ hydroxyalkyls or $C_2$-$C_{18}$ alkoxyalkyls, polyalkylene glycols;
or a group of formula (III)

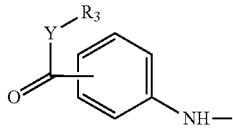

wherein Y, independently of the value of X, is an —O— or —NH— group
$R_3$ is a straight, cyclic or branched $C_1$-$C_{18}$ alkyl group which is the same or different from R;
or a group of formula (IV)

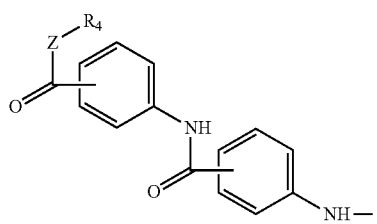

wherein Z, independently of the value of X and Y, is an —O— or —NH— group $R_4$ is a straight, cyclic or branched $C_1$-$C_{18}$ alkyl group which is the same or different from R and $R_3$;
b) at least one other UV filter selected from 2-ethyhexyl p-methoxycinnamate, 2-hydroxy-4-methoxybenzophenone, 2-hydroxy-4-methoxybenzophenone-5-sulphonic acid, ethylhexyl salicylate, ethylhexyl dimethyl PABA, drometrizole trisiloxane, 3-(4'-methylbenzylidene)-d,l-camphor, diethylhexyl butamido triazone, ethylhexyl triazone, 4-(tert-butyl)-4'-methoxy-dibenzoylmethane, 2-cyano-3,3-diphenylacrylic acid 2-ethylhexyl ester, bis-ethylhexyloxyphenol-methoxyphenyltriazine, methylene-bis-benzotriazolyl-tetramethylbutylphenol, benzoic acid 2-(4-diethylamino-2-hydroxybenzoyl)-hexyl ester, 2,4-bis-[4-[5-(1,1-dimethyl-propyl)benzoxazol-2-yl [phenylimino]-6-[(2-ethylhexyl)imino]-1,3,5-triazine, tris-biphenyltriazine, titanium dioxide and zinc oxide;
c) optionally other components selected from the group consisting of solvents, diluents, auxiliaries and cosmetic carriers.

2. Compositions according to claim 1 wherein component (a) consists of one or more compounds of formula (I) wherein the —CONH—, —CO—XR, —CO—$YR_3$, and —CO—$ZR_4$ groups on the phenyl rings are in the para position relative to the —NH— group, and the R, R1, R2, R3, and R4 groups are straight or branched $C_1$-$C_{12}$ alkyl groups.

3. Compositions according to claim 1 wherein component (a) is selected from the compounds of formula (V), (VI) and (VII)

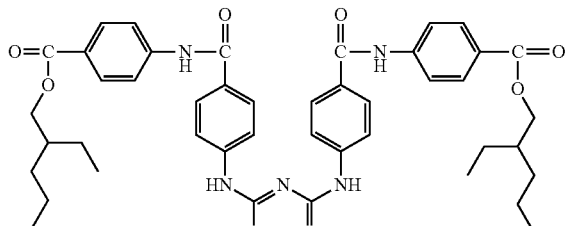

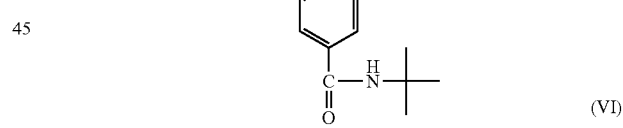

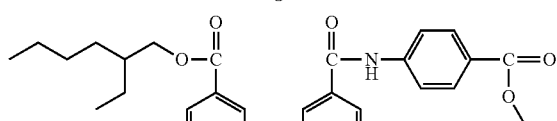

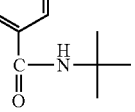

-continued (VII)

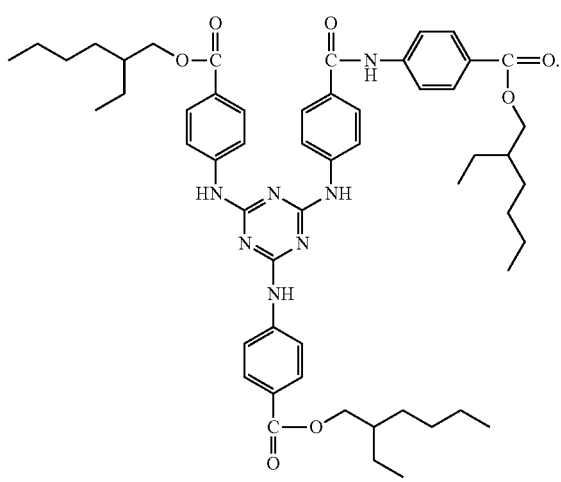

4. Compositions according to claim 1 wherein component a) has a UVA/UVB ratio greater than 0.20.

5. Compositions according to claim 1 wherein component (b) is 4-(tert-butyl)-4'-methoxy-dibenzoylmethane, 2-cyano-3,3-diphenylacrylic acid 2-ethylhexyl ester, diethylhexyl butamido triazone, ethylhexyl triazone, bis-ethylhexyl-oxyphenol-methoxyphenyl-triazine, methylene-bis-benzotriazolyl-tetramethylbutyl-phenol, or benzoic acid 2-(4-diethyl-amino-2-hydroxybenzoyl)-hexyl ester.

6. A method for protecting the skin or hair or both from solar UV radiation, which comprises administration to the skin or hair or both of a cosmetic composition of:

(a) at least one UV filter of formula (I), (I)

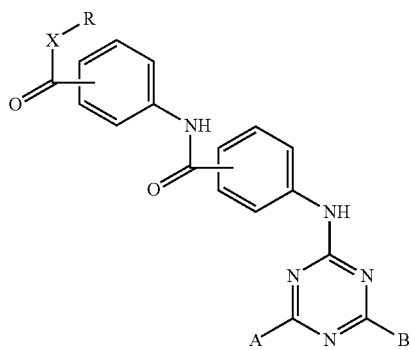

wherein:
X is an —O— or NH— group
R is a straight, cyclic, or branched $C_1$-$C_{18}$ alkyl group
and groups A and B are, independently of one another:
a group of formula (II)

(II)

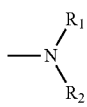

wherein $R_1$ and $R_2$ are, independently of one another, H, straight, cyclic or branched $C_1$-$C_{22}$ alkyls or $C_1$-$C_{18}$ hydroxyalkyls or $C_2$-$C_{18}$ alkoxyalkyls, or polyalkylene glycols;
or a group of formula (III)

(III)

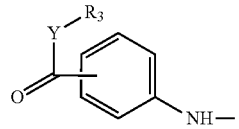

wherein Y, independently of the value of X, is an —O— or NH— group
R3 is a straight, cyclic, or branched $C_1$-$C_{18}$ alkyl group which is the same or different from R;
or a group of formula (IV)

(IV)

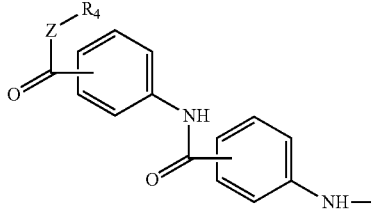

wherein Z, independently of the value of X and Y, is an —O— or —NH— group
R4 is a straight, cyclic or branched $C_1$-$C_{18}$ alkyl group which is the same or different from R and R3;

(b) at least one other UV filter selected from 2-ethylhexyl p-methoxycinnamate, 2-hydroxy-4-methoxybenzophenone, 2-hydroxy-4-methoxybenzophenone-5-sulphonic acid, ethylhexyl salicylate, ethylhexyl dimethyl PABA, drometrizole trisiloxane, 3-(4'-methylbenzylidene)-d,l-camphor, diethylhexyl butamido triazone, ethylhexyl triazone, 4-(tert-butyl)-4'-methoxy-dibenzoylmethane, 2-cyano-3,3-diphenylacrylic acid 2-ethylhexyl ester, bis-ethylhexyloxyphenol-methoxyphenyl-triazine, methylene-bis-benzotriazolyl-tetramethylbutylphenol, benzoic acid 2-(4-diethylamino-2-hydroxybenzoyl)-hexyl ester, 2,4-bis-[4-[5-(1,1-dimethyl-propyl)benzoxazol-2-yl [phenylimino]-6-[(2-ethylhexyl)-imino]-1,3,5-triazine, tris-biphenyltriazine, titanium dioxide and zinc oxide;

and wherein the concentration of components (a) and (b) is up to 20% by weight of said cosmetic composition.

7. A method for protecting the skin or hair or both from solar UV radiation, which comprises administration to the skin or hair or both of a cosmetic composition of:

(a) at least one UV filter of formula (I),

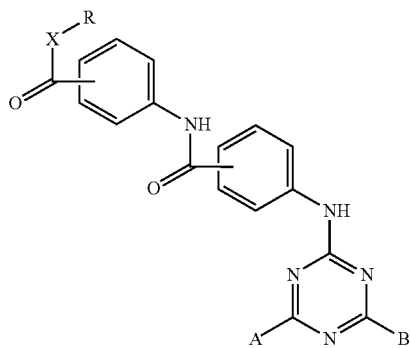

(I)

wherein:
X is an —O— or —NH— group
R is a straight, cyclic, or branched $C_1$-$C_{18}$ alkyl group
and groups A and B are, independently of one another:
a group of formula (II)

(II)

wherein $R_1$ and $R_2$ are, independently of one another, H, straight, cyclic or branched $C_1$-$C_{22}$ alkyls or $C_1$-$C_{18}$ hydroxyalkyls or $C_2$-$C_{18}$ alkoxyalkyls, or polyalkylene glycols;
or a group of formula (III)

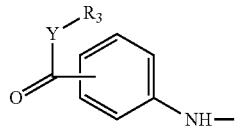

(III)

wherein Y, independently of the value of X, is an —O— or —NH— group

R3 is a straight, cyclic, or branched $C_1$-$C_{18}$ alkyl group which is the same or different from R;

or a group of formula (IV)

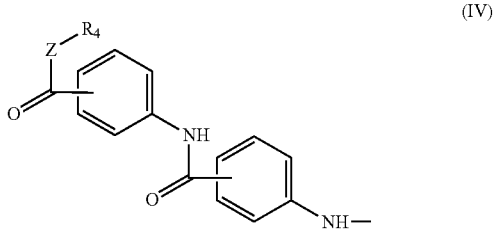

(IV)

wherein Z, independently of the value of X and Y, is an —O— or —NH— group

R4 is a straight, cyclic or branched $C_1$-$C_{18}$ alkyl group which is the same or different from R and R3;

(b) at least one other UV filter selected from 4-(tert-butyl)-4'-methoxy-dibenzoylmethane, 2-cyano-3,3-diphenylacrylic acid 2-ethylhexyl ester, diethylhexyl butamido triazone, ethylhexyl triazone, bis-ethylhexyloxyphenol-methoxyphenyl-triazine, methylene-bis-benzotriazolyl-tetramethylbutylphenol, and benzoic acid 2-(4-diethylamino-2-hydroxybenzoyl)-hexyl ester;

and in which the concentration of the components (a) and (b) is up to 20% by weight of the above-said cosmetic composition.

* * * * *